United States Patent
Ruiz et al.

(10) Patent No.: US 7,717,908 B2
(45) Date of Patent: *May 18, 2010

(54) METHOD PATTERNS FOR INTRASTROMAL REFRACTIVE SURGERY

(75) Inventors: Luis Antonio Ruiz, Bogotá (CO); Josef F. Bille, Heidelberg (DE)

(73) Assignee: Technolas Perfect Vision GmbH, Heidelberg (DE)

( * ) Notice: Subject to any disclaimer, the term of this patent is extended or adjusted under 35 U.S.C. 154(b) by 0 days.

This patent is subject to a terminal disclaimer.

(21) Appl. No.: 12/105,195

(22) Filed: Apr. 17, 2008

(65) Prior Publication Data

US 2009/0157063 A1    Jun. 18, 2009

Related U.S. Application Data

(63) Continuation-in-part of application No. 11/958,202, filed on Dec. 17, 2007.

(51) Int. Cl.
    *A61F 9/008* (2006.01)
(52) U.S. Cl. .............. 606/5; 128/898; 606/3; 606/4; 606/11
(58) Field of Classification Search ........ 606/5
    See application file for complete search history.

(56) References Cited

U.S. PATENT DOCUMENTS

| | | |
|---|---|---|
| 4,391,275 A | 7/1983 | Fankhauser et al. |
| 4,665,913 A | 5/1987 | L'Esperance, Jr. |
| 4,669,466 A * | 6/1987 | L'Esperance ........... 606/3 |
| 4,718,418 A | 1/1988 | L'Esperance, Jr. |
| 4,721,379 A | 1/1988 | L'Esperance |
| 4,732,148 A | 3/1988 | L'Esperance, Jr. |
| 4,770,172 A | 9/1988 | L'Esperance, Jr. |
| 4,907,586 A | 3/1990 | Bille et al. |
| 4,988,348 A | 1/1991 | Bille |
| 5,533,997 A | 7/1996 | Ruiz |
| 5,549,632 A | 8/1996 | Lai |
| 5,928,129 A | 7/1999 | Ruiz |
| 5,984,916 A | 11/1999 | Lai |
| 5,993,438 A | 11/1999 | Juhasz et al. |
| 6,110,166 A | 8/2000 | Juhasz |
| 6,231,566 B1 | 5/2001 | Lai |
| 6,302,877 B1 | 10/2001 | Ruiz |
| 6,325,792 B1 | 12/2001 | Swinger et al. |

(Continued)

OTHER PUBLICATIONS

Heisterkamp et al., "Intrastromal Refractive Surgery With Ultrashort Laser Pulses: In Vivo Study On The Rabbit Eye", Laboratory Investigation, (2002), pp. 511-515.

(Continued)

*Primary Examiner*—Henry M Johnson, III
*Assistant Examiner*—Jeffrey Lipitz
(74) *Attorney, Agent, or Firm*—Nydegger & Associates (57) ABSTRACT

A method for performing intrastromal ophthalmic laser surgery requires Laser Induced Optical Breakdown (LIOB) of stromal tissue without compromising Bowman's capsule (membrane). In detail, the method creates cuts in the stroma along planes radiating from the visual axis of the eye. Importantly, these cuts are all distanced from the visual axis. The actual location and number of cuts in the surgery will depend on the degree of visual aberration being corrected. Further, the method may include the additional step of creating cylindrical cuts in the stroma. The radial cuts and cylindrical cuts may be intersecting or non-intersecting depending on the visual aberration being treated.

20 Claims, 4 Drawing Sheets

U.S. PATENT DOCUMENTS

| | | | |
|---|---|---|---|
| 6,607,527 | B1 | 8/2003 | Ruiz et al. |
| 6,610,051 | B2 | 8/2003 | Bille |
| 6,635,051 | B1 * | 10/2003 | Hohla .................. 606/5 |
| 6,843,787 | B2 | 1/2005 | Ruiz |
| 6,902,561 | B2 * | 6/2005 | Kurtz et al. .................. 606/4 |
| 2002/0193704 | A1 | 12/2002 | Goldstein et al. |
| 2003/0003295 | A1 | 1/2003 | Dreher et al. |
| 2003/0212387 | A1 * | 11/2003 | Kurtz et al. ................ 606/4 |
| 2004/0044355 | A1 * | 3/2004 | Nevyas .................. 606/166 |
| 2004/0243112 | A1 * | 12/2004 | Bendett et al. .............. 606/5 |
| 2005/0149006 | A1 * | 7/2005 | Peyman ...................... 606/5 |
| 2006/0015090 | A1 * | 1/2006 | Roberts et al. .............. 606/5 |
| 2006/0106372 | A1 * | 5/2006 | Kuhn et al. ................ 606/5 |

OTHER PUBLICATIONS

Juhasz, et al., "Corneal Refractive Surgery With Femtosecond Lasers", IEEE Journal of Selected Topics In Quantum Electronics, (Jul./Aug. 1999), vol. 5, No. 4.

\* cited by examiner

METHOD PATTERNS FOR INTRASTROMAL REFRACTIVE SURGERY

This application is a continuation-in-part of application Ser. No. 11/958,202 filed Dec. 17, 2007, which is currently pending. The contents of application Ser. No. 11/958,202 are incorporated herein by reference.

FIELD OF THE INVENTION

The present invention pertains generally to methods for performing intrastromal ophthalmic laser surgery. More particularly, the present invention pertains to laser surgery wherein stromal tissue is cut on concentric cylindrical surfaces, with the surfaces being oriented parallel to, and centered on, the visual axis of an eye. The present invention is particularly, but not exclusively, useful as a method for performing intrastromal ophthalmic laser surgery wherein reshaping of the cornea is accomplished by inducing a redistribution of bio-mechanical forces in the cornea.

BACKGROUND OF THE INVENTION

The cornea of an eye has five (5) different identifiable layers of tissue. Proceeding in a posterior direction from the anterior surface of the cornea, these layers are: the epithelium; Bowman's capsule (membrane); the stroma; Descemet's membrane; and the endothelium. Behind the cornea is an aqueous-containing space called the anterior chamber. Importantly, pressure from the aqueous in the anterior chamber acts on the cornea with bio-mechanical consequences. Specifically, the aqueous in the anterior chamber of the eye exerts an intraocular pressure against the cornea. This creates stresses and strains that place the cornea under tension.

Structurally, the cornea of the eye has a thickness (T), that extends between the epithelium and the endothelium. Typically, "T" is approximately five hundred microns (T=500 µm). From a bio-mechanical perspective, Bowman's capsule and the stroma are the most important layers of the cornea. Within the cornea, Bowman's capsule is a relatively thin layer (e.g. 20 to 30 µm) that is located below the epithelium, within the anterior one hundred microns of the cornea. The stroma then comprises almost all of the remaining four hundred microns in the cornea. Further, the tissue of Bowman's capsule creates a relatively strong, elastic membrane that effectively resists forces in tension. On the other hand, the stroma comprises relatively weak connective tissue.

Bio-mechanically, Bowman's capsule and the stroma are both significantly influenced by the intraocular pressure that is exerted against the cornea by aqueous in the anterior chamber. In particular, this pressure is transferred from the anterior chamber, and through the stroma, to Bowman's membrane. It is known that how these forces are transmitted through the stroma will affect the shape of the cornea. Thus, by disrupting forces between interconnective tissue in the stroma, the overall force distribution in the cornea can be altered. Consequently, this altered force distribution will then act against Bowman's capsule. In response, the shape of Bowman's capsule is changed, and due to the elasticity and strength of Bowman's capsule, this change will directly influence the shape of the cornea. With this in mind, and as intended for the present invention, refractive surgery is accomplished by making cuts on predetermined surfaces in the stroma to induce a redistribution of bio-mechanical forces that will reshape the cornea.

It is well known that all of the different tissues of the cornea are susceptible to Laser Induced Optical Breakdown (LIOB).

Further, it is known that different tissues will respond differently to a laser beam, and that the orientation of tissue being subjected to LIOB may also affect how the tissue reacts to LIOB. With this in mind, the stroma needs to be specifically considered.

The stroma essentially comprises many lamellae that extend substantially parallel to the anterior surface of the eye. In the stroma, the lamellae are bonded together by a glue-like tissue that is inherently weaker than the lamellae themselves. Consequently, LIOB over layers parallel to the lamellae can be performed with less energy (e.g. 0.8 µJ) than the energy required for the LIOB over cuts that are oriented perpendicular to the lamellae (e.g. 1.2 µJ). It will be appreciated by the skilled artisan, however, that these energy levels are only exemplary. If tighter focusing optics can be used, the required energy levels will be appropriately lower. In any event, depending on the desired result, it may be desirable to make only cuts in the stroma. On the other hand, for some procedures it may be more desirable to make a combination of cuts and layers.

In light of the above, it is an object of the present invention to provide methods for performing ophthalmic laser surgery that result in reshaping the cornea to achieve refractive corrections for improvement of a patient's vision. Another object of the present invention is to provide methods for performing ophthalmic laser surgery that require minimal LIOB of stromal tissue. Still another object of the present invention is to provide methods for performing ophthalmic laser surgery that avoid compromising Bowman's capsule and, instead, maintain it intact for use in providing structural support for a reshaped cornea. Yet another object of the present invention is to provide methods for performing ophthalmic laser surgery that are relatively easy to implement and comparatively cost effective.

SUMMARY OF THE INVENTION

In accordance with the present invention, methods for performing intrastromal ophthalmic laser surgery are provided that cause the cornea to be reshaped under the influence of bio-mechanical forces. Importantly, for these methods, a tissue volume for operation is defined that is located solely within the stroma of the cornea. Specifically, this operational volume extends posteriorly from slightly below Bowman's capsule (membrane) to a substantial depth into the stroma that is equal to approximately nine tenths of the thickness of the cornea. Thus, with the cornea having a thickness "T" (e.g. approximately 500 µm), the operational volume extends from below Bowman's capsule (e.g. 100 µm) to a depth in the cornea that is equal to approximately 0.9 T (e.g. approximately 450 µm). Further, the operational volume extends radially from the visual axis of the eye through a distance of about 5.0 mm (i.e. the operational volume has a diameter of around 10.0 mm).

In general, each method of the present invention requires the use of a laser unit that is capable of generating a so-called femtosecond laser beam. Stated differently, the duration of each pulse in the beam will approximately be less than one picosecond. When generated, this beam is directed and focused onto a series of focal spots in the stroma. The well-known result of this is a Laser Induced Optical Breakdown (LIOB) of stromal tissue at each focal spot. In particular, and as intended for the present invention, movement of the focal spot in the stroma creates a plurality of cuts. Such cuts may include a pattern of radial cuts, or a pattern of radial cuts and cylindrical cuts. Specifically, the radial cuts will be located at a predetermined azimuthal angle θ and will be substantially coplanar with the visual axis of the eye. Each radial cut will be in the operational volume described above and will extend outwardly from the visual axis from an inside radius "$r_i$" to an outside radius "$r_o$". Further, there may be as many "radial cuts" as desired, with each "radial cut" having its own specific azimuthal angle θ.

Geometrically, the cylindrical cuts are made on portions of a respective cylindrical surface. These respective cylindrical surfaces on which cylindrical cuts are made are concentric, and they are centered on the visual axis of the eye. And, they can be circular cylinders or oval (elliptical) cylinders. Further each cylindrical surface has an anterior end and a posterior end. To maintain the location of the cylindrical surface within the operational volume, the posterior end of the cylindrical cut is located no deeper in the stroma than approximately 0.9 T from the anterior surface of the eye. On the other hand, the anterior end of the cylindrical cut is located in the stroma more than at least eight microns in a posterior direction from Bowman's capsule. These cuts will each have a thickness of about two microns.

In a preferred procedure, each cylindrical cut is approximately two hundred microns from an adjacent cut, and the innermost cylindrical cut (i.e. center cylindrical cut) may be located about 1.0 millimeters from the visual axis. There can, of course be many such cylindrical cuts (preferably five), and they can each define a substantially complete cylindrical shaped wall. Such an arrangement may be particularly well suited for the treatment of presbyopia. In a variant of this procedure that would be more appropriate for the treatment of astigmatism, portions of the cylindrical surfaces subjected to LIOB can define diametrically opposed arc segments. In this case each arc segment preferably extends through an arc that is in a range between five degrees and one hundred and sixty degrees. Insofar as the cuts are concerned, each pulse of the laser beam that is used for making the cut has an energy of approximately 1.2 microJoules or, perhaps, less (e.g. 1.0 microJoules).

For additional variations in the methods of the present invention, in addition to or instead of the cuts mentioned above, differently configured layers of LIOB can be created in the stromal tissue of the operational volume. To create these layers, LIOB is performed in all, or portions, of an annular shaped area. Further, each layer will lie in a plane that is substantially perpendicular to the visual axis of the eye. For purposes of the present invention the layers are distanced approximately ten microns from each adjacent layer, and each layer will have an inner diameter "$d_i$", and an outer diameter "$d_o$". These "layers" will have a thickness of about one micron. As indicated above, the present invention envisions creating a plurality of such layers adjacent to each other, inside the operational volume.

As intended for the present invention, all "cuts" and "layers" (i.e. the radial cuts, cylindrical cuts, and the annular layers) will weaken stromal tissue, and thereby cause a redistribution of bio-mechanical forces in the stroma. Specifically, weaknesses in the stroma that result from the LIOB of "cuts" and "layers" will respectively cause the stroma to "bulge" or "flatten" in response to the intraocular pressure from the anterior chamber. As noted above, however, these changes will be somewhat restrained by Bowman's capsule. The benefit of this restraint is that the integrity of the cornea is maintained. Note: in areas where layers are created, there can be a rebound of the cornea that eventually results in a slight bulge being formed. Regardless, with proper prior planning, the entire cornea can be bio-mechanically reshaped, as desired.

With the above in mind, it is clear the physical consequences of making "cuts" or "layers" in the stroma are somewhat different. Although they will both weaken the stroma, to thereby allow intraocular pressure from aqueous in the anterior chamber to reshape the cornea, "cuts" (i.e. LIOB parallel and radial to the visual axis) will cause the cornea to bulge. On the other hand, "layers" (i.e. LIOB perpendicular to the visual axis) will tend to flatten the cornea. In any event. "cuts," alone, or a combination of "cuts" with "layers" can be used to reshape the cornea with only an insignificant amount of tissue removal.

In accordance with the present invention, various procedures can be customized to treat identifiable refractive imperfections. Specifically, in addition to cuts alone, the present invention contemplates using various combinations of cuts and layers. In each instance, the selection of cuts, or cuts and layers, will depend on how the cornea needs to be reshaped. Also, in each case it is of utmost importance that the cuts and layers be centered on the visual axis (i.e. there must be centration). Some examples are:

Presbyopia: Cylindrical cuts only need be used for this procedure.

Myopia: A pattern of radial cuts with any cylindrical cuts may be used. If used, the radial cuts are each made with their respective azimuthal angle θ, inside radius "$r_i$" and outside radius "$r_o$", all predetermined. Further, a combination of cylindrical cuts (circular or oval) and annular layers can be used without radial cuts. In this case a plurality of cuts is distanced from the visual axis beginning at a radial distance "$r_c$", and a plurality of layers is located inside the cuts. Specifically, "$d_i$" of the plurality of layers can be zero (or exceedingly small), and "$d_o$" of the plurality of layers can be less than $2r_c$ ($d_0 < 2r_c$). In an alternative procedure, radial cuts can be employed alone, or in combination with cylindrical cuts and annular layers.

Hyperopia: A combination of cylindrical cuts and annular layers can be used. In this case, the plurality of cuts is distanced from the visual axis in a range between and inner radius "$r_{ci}$" and an outer radius "$r_{co}$", wherein $r_{co} > r_{ci}$, and further wherein "$d_i$" of the plurality of layers is greater than $2r_{co}$ ($d_o > d_i > 2r_{co}$).

Astigmatism: Cylindrical cuts can be used alone, or in combination with annular layers. Specifically arc segments of cylindrical cuts are oriented on a predetermined line that is perpendicular to the visual axis. Layers can then be created between the arc segments.

Myopic astigmatism: Cylindrical cuts formed along an arc segment may be used with a pattern of radial cuts. Depending on the required correction, the radial and cylindrical cuts may be intersecting or non-intersecting.

Whenever a combination of cuts and layers are required, the energy for each pulse that is used to create the cylindrical cuts will be approximately 1.2 microJoules. On the other hand, as noted above, the energy for each pulse used to create an annular layer will be approximately 0.8 microJoules.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENTS

Figure 1:
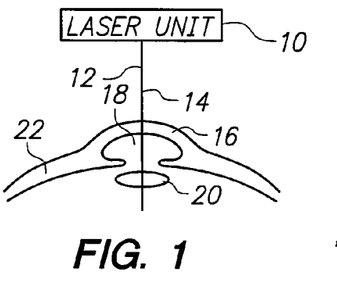
FIG. 1 is a cross-sectional view of the cornea of an eye shown in relationship to a schematically depicted laser unit.

Referring initially to FIG. 1, it will be seen that the present invention includes a laser unit 10 for generating a laser beam 12. More specifically, the laser beam 12 is preferably a pulsed laser beam, and the laser unit 10 generates pulses for the beam 12 that are less than one picosecond in duration (i.e. they are femtosecond pulses). In FIG. 1, the laser beam 12 is shown being directed along the visual axis 14 and onto the cornea 16 of the eye. Also shown in FIG. 1 is the anterior chamber 18 of the eye that is located immediately posterior to the cornea 16. There is also a lens 20 that is located posterior to both the anterior chamber 18 and the sclera 22.

Figure 2:
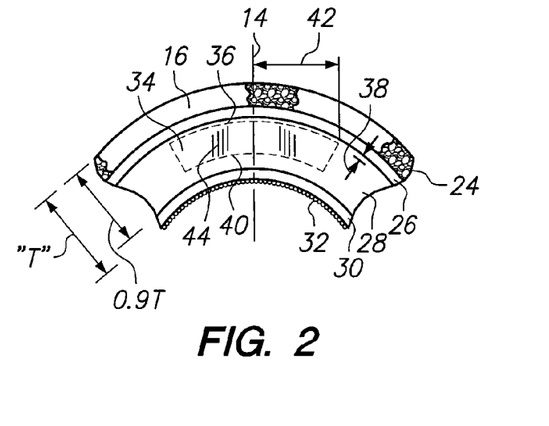
FIG. 2 is a cross-sectional view of the cornea showing a defined operational volume in accordance with the present invention.

In FIG. 2, five (5) different anatomical tissues of the cornea 16 are shown. The first of these, the epithelium 24 defines the anterior surface of the cornea 16. Behind the epithelium 24, and ordered in a posterior direction along the visual axis 14, are Bowman's capsule (membrane) 26, the stroma 28, Descemet's membrane 30 and the endothelium 32. Of these tissues, Bowman's capsule 26 and the stroma 28 are the most important for the present invention. Specifically, Bowman's capsule 26 is important because it is very elastic and has superior tensile strength. It therefore, contributes significantly to maintaining the general integrity of the cornea 16.

For the methods of the present invention, Bowman's capsule 26 must not be compromised (i.e. weakened). On the other hand, the stroma 28 is intentionally weakened. In this case, the stroma 28 is important because it transfers intraocular pressure from the aqueous in the anterior chamber 18 to Bowman's membrane 26. Any selective weakening of the stroma 28 will therefore alter the force distribution in the stroma 28. Thus, as envisioned by the present invention, LIOB in the stroma 28 can be effectively used to alter the force distribution that is transferred through the stroma 28, with a consequent reshaping of the cornea 16. Bowman's capsule 26 will then provide structure for maintaining a reshaped cornea 16 that will effectively correct refractive imperfections.

While referring now to FIG. 2, it is to be appreciated that an important aspect of the present invention is an operational volume 34 which is defined in the stroma 28. Although the operational volume 34 is shown in cross-section in FIG. 2, this operational volume 34 is actually three-dimensional, and extends from an anterior surface 36 that is located at a distance 38 below Bowman's capsule 26, to a posterior surface 40 that is located at a depth 0.9 T in the cornea 16. Both the anterior surface 36 and the posterior surface 40 essentially conform to the curvature of the stroma 28. Further, the operational volume 34 extends between the surfaces 36 and 40 through a radial distance 42. For a more exact location of the anterior surface 36 of the operational volume, the distance 38 will be greater than about eight microns. Thus, the operational volume 34 will extend from a depth of about one hundred microns in the cornea 16 (i.e. a distance 38 below Bowman's capsule 26) to a depth of about four hundred and fifty microns (i.e. 0.9T). Further, the radial distance 42 will be approximately 5.0 millimeters.

Figure 3:
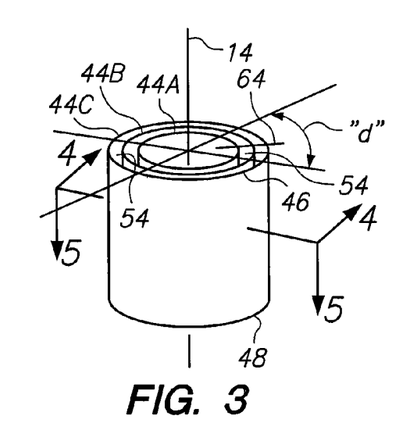
FIG. 3 is a perspective view of a plurality of cylindrical surfaces where laser cuts can be made by LIOB.

FIG. 3 illustrates a plurality of cuts 44 envisioned for the present invention. As shown, the cuts 44a, 44b and 44c are only exemplary, as there may be more or fewer cuts 44, depending on the needs of the particular procedure. With this in mind, and for purposes of this disclosure, the plurality will sometimes be collectively referred to as cuts 44.

Figure 4:
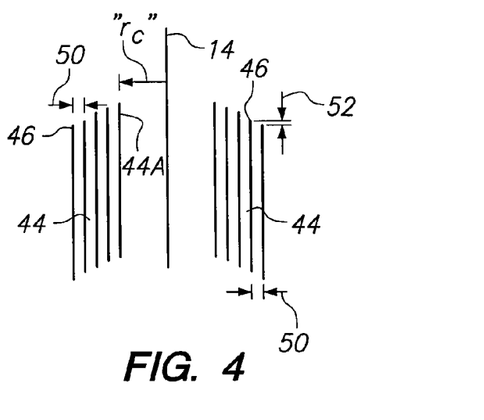
FIG. 4 is a cross-sectional view of cuts on the plurality of cylindrical surfaces, as seen along the line 4-4 in FIG. 3, with the cuts shown for a typical treatment of presbyopia.
Figure 5A:
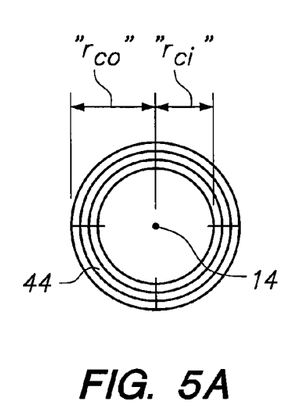
FIG. 5A is a cross-sectional view of the plurality of cylindrical surfaces as seen along the line 5-5 in FIG. 3 when complete cuts have been made on the cylindrical surfaces.

As shown in FIG. 3, the cuts 44 are made on respective cylindrical surfaces. Although the cuts 44 are shown as circular cylindrical surfaces, these surfaces may be oval. When the cuts 44 are made in the stroma 28, it is absolutely essential they be confined within the operational volume 34. With this in mind, it is envisioned that cuts 44 will be made by a laser process using the laser unit 10. And, that this process will result in Laser Induced Optical Breakdown (LIOB). Further, it is important these cylindrical surfaces be concentric, and that they are centered on an axis (e.g. the visual axis 14). Further, each cut 44 has an anterior end 46 and a posterior end 48. As will be best appreciated by cross-referencing FIG. 3 with FIG. 4, the cuts 44 (i.e. the circular or oval cylindrical surfaces) have a spacing 50 between adjacent cuts 44. Preferably, this spacing 50 is equal to approximately two hundred microns. FIG. 4 also shows that the anterior ends 46 of respective individual cuts 44 can be displaced axially from each other by a distance 52. Typically, this distance 52 will be around ten microns. Further, the innermost cut 44 (e.g. cut 44a shown in FIG. 4) will be at a radial distance "$r_c$" that will be about 1 millimeter from the visual axis 14. From another perspective, FIG. 5A shows the cuts 44 centered on the visual axis 14 to form a plurality of rings. In this other perspective, the cuts 44 collectively establish an inner radius "$r_{ci}$" and an outer radius "$r_{co}$". Preferably, each cut 44 will have a thickness of about two microns, and the energy required to make the cut 44 will be approximately 1.2 microJoules.

Figure 5B:
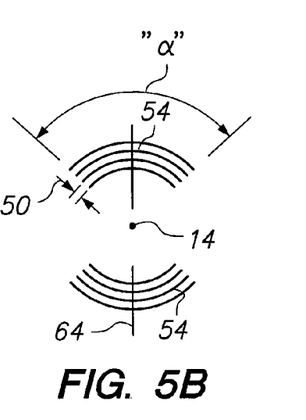
FIG. 5B is a cross-sectional view of the plurality of cylindrical surfaces as seen along the line 5-5 in FIG. 3 when partial cuts have been made along arc segments on the cylindrical surfaces for the treatment of astigmatism.

As an alternative to the cuts 44 disclosed above, FIG. 3 indicates that only arc segments 54 may be used, if desired. Specifically, in all essential respects, the arc segments 54 are identical with the cuts 44. The exception, however, is that they are confined within diametrically opposed arcs identified in FIGS. 3 and 5B by the angle "α". More specifically, the result is two sets of diametrically opposed arc segments 54. Preferably, "α" is in a range between five degrees and one hundred and sixty degrees.

Figure 5C:
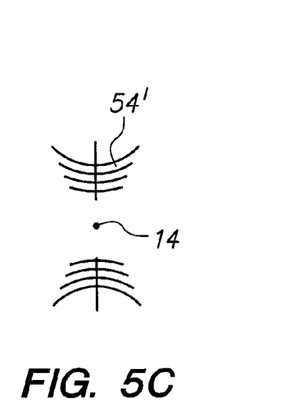
FIG. 5C is a cross-sectional view of an alternate embodiment for cuts made similar to those shown in FIG. 5B and for the same purpose.

An alternate embodiment for the arc segments 54 are the arc segments 54' shown in FIG. 5C. There it will be seen that the arc segments 54' like the arc segments 54 are in diametrically opposed sets. The arc segments 54', however, are centered on respective axes (not shown) that are parallel to each other, and equidistant from the visual axis 14.

Figure 6:
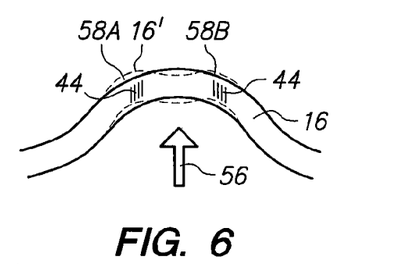
FIG. 6 is a cross-sectional view of a cornea showing the bio-mechanical consequence of making cuts in the cornea in accordance with the present invention.

FIG. 6 provides an overview of the bio-mechanical reaction of the cornea 16 when cuts 44 have been made in the operational volume 34 of the stroma 28. As stated above, the cuts 44 are intended to weaken the stroma 28. Consequently, once the cuts 44 have been made, the intraocular pressure (represented by arrow 56) causes a change in the force distribution within the stroma 28. This causes bulges 58a and 58b that result in a change in shape from the original cornea 16 into a new configuration for cornea 16', represented by the dashed lines. As intended for the present invention, this results in refractive corrections for the cornea 16 that improves vision.

Figure 7:
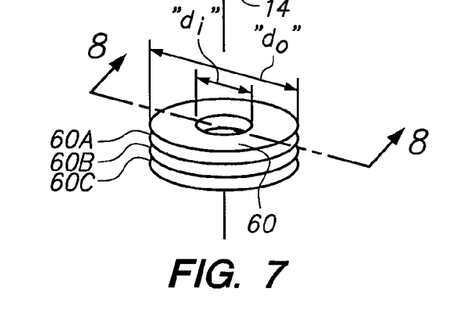
FIG. 7 is a perspective view of a plurality of layers produced by LIOB in accordance with the present invention.

In addition to the cuts 44 disclosed above, the present invention also envisions the creation of a plurality of layers 60 that, in conjunction with the cuts 44, will provide proper vision corrections. More specifically, insofar as the layers 60 are concerned, FIG. 7 shows they are created on substantially flat annular shaped surfaces that collectively have a same inner diameter "$d_i$" and a same outer diameter "$d_o$". It will be appreciated, however, that variations from the configurations shown in FIG. 7 are possible. For example, the inner diameter "$d_i$" may be zero. In that case the layers are disk-shaped. On the other hand, the outer diameter "$d_o$" may be as much as 8.0 millimeters. Further, the outer diameter "$d_o$" may be varied from layer 60a, to layer 60b, to layer 60c etc.

Figure 8:
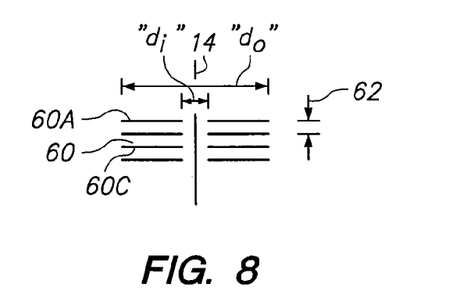
FIG. 8 is a cross-sectional view of the layers as seen along the line 8-8 in FIG. 7.

From a different perspective, FIG. 8 shows that the layers 60 can be stacked with a separation distance 62 between adjacent layers 60 equal to about ten microns. Like the cuts 44 disclosed above, each layer 60 is approximately one micron thick. As mentioned above, the energy for LIOB of the layers 60 will typically be less than the laser energy required to create the cuts 44. In the case of the layers 60 the laser energy for LIOB of the cuts 44 will be approximately 0.8 microJoules.

Figure 9A:
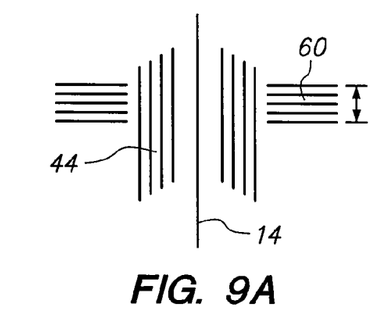
FIG. 9A is a cross-sectional view of a combination of cuts and layers as seen in a plane containing the visual axis of the eye, with the combination arranged for a treatment of hyperopia.
Figure 9B:
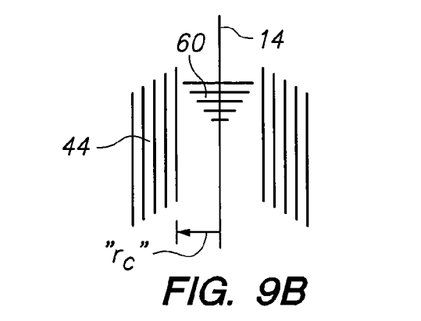
FIG. 9B is a cross-sectional view of a combination of cuts and layers as seen in a plane containing the visual axis of the eye, with the combination arranged for a treatment of myopia.
Figure 9C:
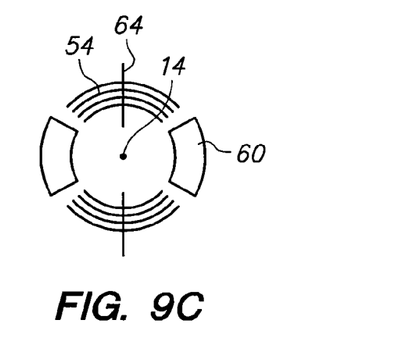
FIG. 9C is a cross-sectional view of a combination of cuts and layers as seen in a plane containing the visual axis of the eye, with the combination arranged for a treatment of astigmatism.

For purposes of the present invention, various combinations of cuts 44 and layers 60, or cuts 44 only, are envisioned. Specifically, examples can be given for the use of cuts 44 and layers 60 to treat specific situations such as presbyopia, myopia, hyperopia and astigmatism. In detail, for presbyopia, a plurality of only cuts 44 needs to be used for this procedure. Preferably, the cuts 44 are generally arranged as shown in FIGS. 4 and 5A. Further, for presbyopia it is typical for there to be five individual cuts 44 that extend from an inner radius of about 1 mm to an outer radius of about 1.8 mm, with a 200 micron separation between adjacent cuts 44. When hyperopia/presbyopia need to be corrected together, the cuts 44 will then preferably extend further to an outer radius of about 2.3 mm. For hyperopia, a combination of cylindrical cuts 44 and annular layers 60 can be used as shown in FIG. 9A. In this case, the plurality of cuts 44 is distanced from the visual axis 14 in a range between and inner radius "$r_{ci}$" (e.g. $r_{ci}$=1 mm) and an outer radius "$r_{co}$" (e.g. $r_{co}$=3 mm), wherein $r_{co} > r_{ci}$, and further wherein "$d_i$" of the plurality of layers 60 is greater than $2r_{co}$ ($d_o > d_i > 2r_{co}$). For myopia, a combination of cylindrical cuts 44 and annular layers 60 can be used as generally shown in FIG. 9B. In this case a plurality of cuts 44 is distanced from the visual axis 14 beginning at a radial distance "$r_c$", and a plurality of layers 60, with decreasing outer diameter "$d_o$" in a posterior direction, is located inside the cuts 44. More specifically, for this case "$d_i$" of the plurality of layers 60 can be zero (or exceedingly small), and "$d_o$" of each layer 60 in the plurality of layers 60 can be less than $2r_c$ ($d_0 < 2r_c$). And finally, for astigmatism, the portions of cylindrical cuts 44 that form arc segments 54 can be used alone (see FIG. 5B and 5C), or in combination with annular layers 60 (see FIG. 9C). Specifically arc segments 54 of cylindrical cuts 44 are oriented on a predetermined line 64 that is perpendicular to the visual axis 14. Layers 60 can then be created between the arc segments 54, if desired (see FIG. 9C).

Figure 9D:
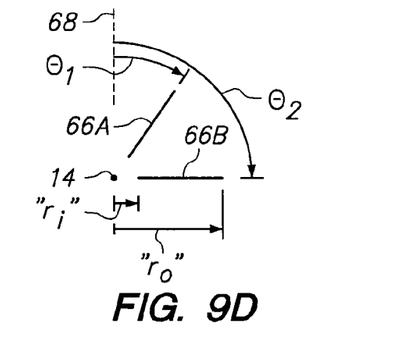
FIG. 9D is a top plan view of radial cuts that are coplanar with the visual axis.

In a variation of the methodologies noted above, the present invention also envisions the creation of radial cuts 66. The radial cuts 66a and 66b shown in FIG. 9D are only exemplary, and are herein sometimes referred to individually or collectively as radial cut(s) 66. Importantly, the radial cuts 66 are coplanar with the visual axis 14, and they are always located within the operational volume 34.

As shown in FIG. 9D, each radial cut 66 is effectively defined by the following parameters: a deepest distance into the stroma 28, $Z_{(distal)}$, a distance below Bowman's capsule 26, $Z_{(proximal)}$, an inner radius, "$r_i$", an outer radius "$r_o$", and an azimuthal angle "θ" that is measured from a base line 68. By setting values for these parameters, each radial cut 66 can be accurately defined. For example, as shown in FIG. 9D, the radial cut 66a is established by the azimuthal angle $θ_1$, while the radial cut 66b has an azimuthal angle $θ_2$. Both of the radial cuts 66a and 66b have the same inner radius "$r_i$" and the same outer radius "$r_o$". The $Z_{(distal)}$ and $Z_{(proximal)}$ will be established for the radial cuts 66a and 66b in a similar manner as described above for the cylindrical cuts 44.

Figure 10:
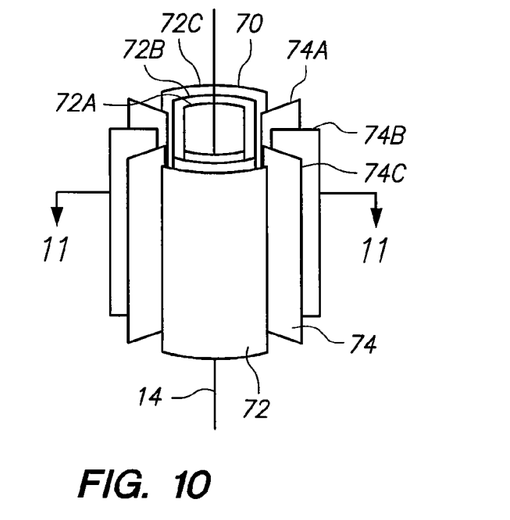
FIG. 10 is a perspective view of a plurality of cylindrical cuts and a pattern of radial cuts made by LIOB.

Referring now to FIG. 10, a plurality of cuts 70 is illustrated for an alternate embodiment of the present invention. Specifically, the plurality of cuts 70 shown is intended to correct a myopic astigmatism. As shown, the plurality of cuts 70 includes the cylindrical cuts 72a, 72b, and 72c and the radial cuts 74a, 74b, and 74c. The cylindrical cuts 72a, 72b, and 72c and the radial cuts 74a, 74b, and 74c are only exemplary, as there may be more or fewer cuts 72, 74, depending on the needs of the particular procedure. As shown in FIG. 10, the cylindrical cuts 72 are made on respective cylindrical surfaces. Although the cylindrical cuts 72 are shown as circular cylindrical surfaces, these surfaces may be oval. It is important these cylindrical surfaces be concentric, and that they are centered on an axis (e.g. the visual axis 14).

Figure 11A:
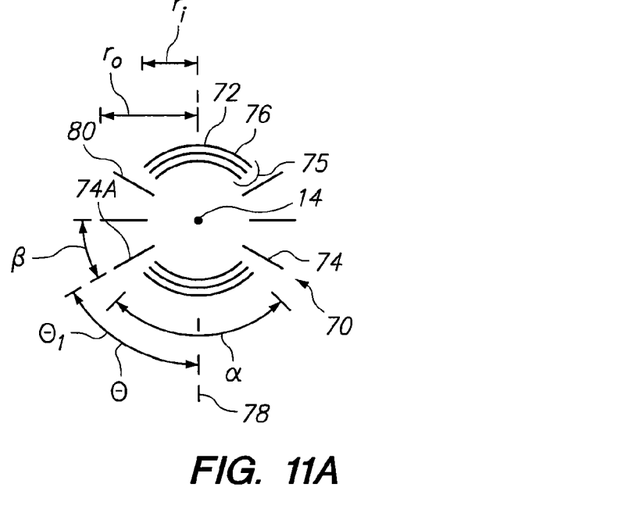
FIG. 11A is a cross-sectional view of the plurality of cylindrical cuts and pattern of radial cuts as seen along the line 11-11 in FIG. 10.

Cross-referencing FIG. 10 with FIG. 11A, it can be seen that the cylindrical cuts 72 are arc segments 76. Specifically, the cylindrical cuts 72 are confined within diametrically opposed arcs identified in FIG. 11A by the angle "α". More specifically, the result is two sets 75 of diametrically opposed arc segments 76. Preferably, "α" is in a range between five degrees and one hundred and sixty degrees. Further, FIG. 11A shows the cuts 72 centered on the visual axis 14. Preferably, each cut 72 will have a thickness of about two microns, and the energy required to make the cut 72 will be approximately 1.2 microJoules.

As further seen in FIG. 11A, the radial cuts 74 are coplanar with the visual axis 14, and they are always located within the operational volume 34 (shown in FIG. 2). Further, each radial cut 74 is effectively defined by the following parameters: an inner radius, "$r_i$", an outer radius "$r_o$", and an azimuthal angle "θ" that is measured from a base line 78. By setting values for these parameters, each radial cut 74 can be accurately defined. For example, as shown in FIG. 11A, the radial cut 74a is established by the azimuthal angle $θ_1$. Each radial cut 74 has the same inner radius "$r_i$" and the same outer radius "$r_o$".

Figure 11B:
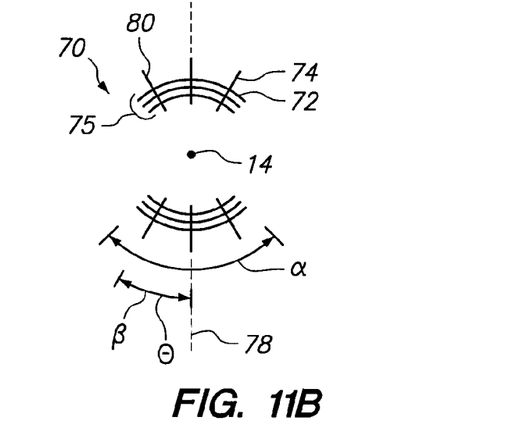
FIG. 11B is a cross-sectional view of a plurality of cylindrical cuts and pattern of radial cuts for an alternative embodiment of the present invention.

While FIGS. 10 and 11A illustrate a plurality of cylindrical cuts 72 and a pattern of radial cuts 74 that do not intersect, the present invention also envisions intersecting cuts 70. As shown in FIG. 11B, the plurality of cylindrical cuts 72 and the pattern of radial cuts 74 do intersect. In each of the embodiments shown in FIGS. 11A and 11B, the radial cuts 74 can be seen to be comprised in two sets 80 which are diametrically opposed from one another. Within each set 80, the radial cuts 74 are distanced from one another by equal angles β. Likewise, the cylindrical cuts 72 also comprise two diametrically opposed sets 75.

Figure 11C:
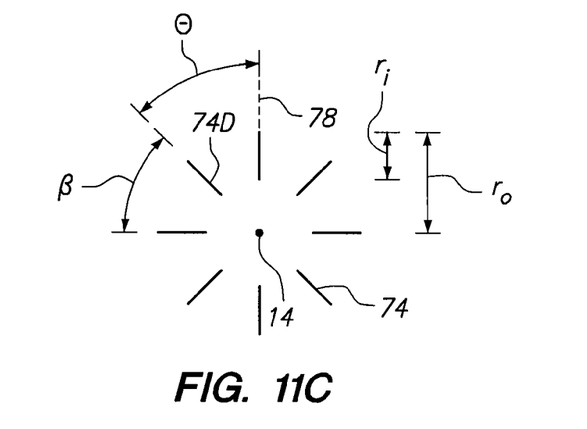
FIG. 11C is a cross-sectional view of a pattern of radial cuts for another alternative embodiment of the present invention.
Figure 11D:
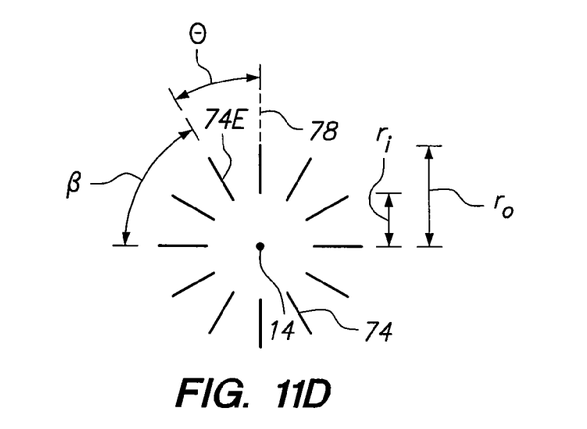
FIG. 11D is a cross-sectional view of a pattern of radial cuts for another alternative embodiment of the present invention.
Figure 11E:
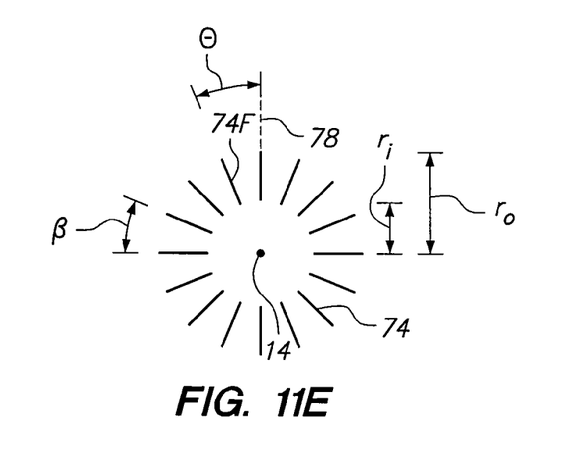
FIG. 11E is a cross-sectional view of a pattern of radial cuts for another alternative embodiment of the present invention.

Referring now to FIGS. 11C, 11D, and 11E, a plurality of radial cuts 74 is illustrated for alternate embodiments of the present invention. In FIG. 11C, eight radial cuts 74 are positioned about the visual axis 14. This pattern of radial cuts 74 is intended for a myopic correction of –0.75 diopters. In FIG. 11D, twelve radial cuts 74 are positioned about the visual axis 14. This pattern of radial cuts 74 is intended for a myopic correction of –1.25 diopters. In FIG. 11E, sixteen radial cuts 74 are positioned about the visual axis 14. This pattern of radial cuts 74 is intended for a myopic correction of –2.0 diopters.

As shown in FIGS. 11C, 11D, and 11E, each radial cut 74 is coplanar with the visual axis 14, and located within the operational volume 34 (shown in FIG. 2). Further, each radial cut 74 is effectively defined by the following parameters: an inner radius, "$r_i$", an outer radius "$r_o$", and an azimuthal angle "θ" that is measured from a base line 78. By setting values for these parameters, each radial cut 74 can be accurately defined. For example, as shown in FIG. 11C, the radial cut 74d is established by the azimuthal angle θ. In FIG. 11D, the radial cut 74e is established by the azimuthal angle θ. Further, in FIG. 11E, the radial cut 74f is established by the azimuthal angle θ.

In FIGS. 11C, 11D, and 11E, each radial cut 74 has the same inner radius "$r_i$" and the same outer radius "$r_o$". In FIG. 11C, each radial cut 74 is distanced from the adjacent radial cut 74 by angle β equal to 45 degrees. Further, in FIG. 11D, each radial cut is distanced from the adjacent radial cut 74 by angle β equal to 30 degrees. In FIG. 11E, each radial cut is distanced from the adjacent radial cut 74 by angle β equal to 22.5 degrees.

While the particular Method Patterns for Intrastromal Refractive Surgery as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A method for performing intrastromal ophthalmic laser surgery, wherein the cornea defines a visual axis and has a thickness "T", and wherein the method comprises the steps of:

generating a pulsed laser beam, wherein the duration of each pulse in the beam is less than approximately one picosecond;

directing and focusing the beam onto a series of focal spots in the stroma for Laser Induced Optical Breakdown (LIOB) of stromal tissue at each focal spot to weaken stromal tissue by redistributing biomechanical forces in the stroma; and moving the focal spot in the stroma to create a pattern of unconnected radial cuts, wherein each radial cut is made coplanar with the visual axis to remove an insignificant amount of tissue to substantially maintain the integrity of the cornea and is defined by an azimuthal angle θ, wherein each radial cut has an anterior end and a posterior end extending from an inner radius "$r_i$" to an outer radius "$r_o$", with both "$r_i$" and "$r_o$" being measured from the visual axis, with the posterior end of each radial cut being located in the stroma within less than approximately 0.9 T from an anterior surface of the eye, and the anterior end of the radial cut is located in the stroma more than at least eight microns in a posterior direction from Bowman's capsule, and further wherein each radial cut has a thickness of approximately two microns, with the weakened stromal tissue being responsive to an intraocular pressure for surgically reshaping the cornea.

2. A method as recited in claim 1 wherein the pattern of radial cuts is formed from eight cuts situated about the visual axis, wherein each cut is 45 degrees from an adjacent cut.

3. A method as recited in claim 1 wherein the pattern of radial cuts is formed from twelve cuts situated about the visual axis, wherein each cut is 30 degrees from an adjacent cut.

4. A method as recited in claim 1 wherein the pattern of radial cuts is formed from sixteen cuts situated about the visual axis, wherein each cut is 22.5 degrees from an adjacent cut.

5. A method as recited in claim 1 wherein the pattern of radial cuts is formed from two sets of at least three cuts, and wherein the sets are diametrically opposed from one another.

6. A method as recited in claim 5 further comprising the step of moving the focal spot in the stroma to create a plurality of cylindrical cuts, wherein each cylindrical cut is made on portions of a respective cylindrical surface, wherein the respective cylindrical surfaces are concentric and are centered on the visual axis of the cornea, and further wherein each cylindrical surface has an anterior end and a posterior end, with the posterior end of each cylindrical cut being located in the stroma less than approximately 0.9 T from an anterior surface of the eye, and with the anterior end of each cylindrical cut being located in the stroma more than at least eight microns in a posterior direction from Bowman's capsule in the cornea.

7. A method as recited in claim 6 wherein the radial cuts intersect the cylindrical cuts.

8. A method as recited in claim 6 wherein the radial cuts and the cylindrical cuts are non-intersecting.

9. A method as recited in claim 6 wherein the portions of the cylindrical surfaces subjected to LIOB define diametrically opposed arc segments wherein each arc segment extends through an arc in a range between five degrees and one hundred and sixty degrees.

10. A method as recited in claim 5 further comprising the steps of:

performing LIOB in portions of an annular layer, wherein the layer has an inner diameter "$d_i$" and an outer diameter "$d_o$", and has a thickness of about one micron;

creating a plurality of layers adjacent to each other; and locating the plurality of layers in the stroma between less than approximately 0.9 T from the anterior surface of the eye and at least eight microns in a posterior direction from Bowman's capsule.

11. A method for performing intrastromal ophthalmic laser surgery wherein the cornea defines a visual axis and has a thickness "T", and wherein the method comprises the steps of:

identifying an operational volume in the stroma, wherein the operational volume is centered on the visual axis and extends radially therefrom through a distance "$r_v$", and further wherein the operational volume has an anterior surface located at least eight microns in a posterior direction from Bowman's capsule (membrane) of the cornea and a posterior surface located at less than approximately 0.9 T from the anterior of the cornea;

focusing a pulsed laser beam to a focal point in the operational volume for LIOB of stromal tissue, wherein each pulse of the laser beam has a duration less than one picosecond to weaken stromal tissue by redistributing biomechanical forces in the stroma; and moving the focal spot within the operational volume to create a pattern of unconnected radial cuts, wherein each radial cut is made coplanar with the visual axis to remove an insignificant amount of tissue to substantially maintain the integrity of the cornea and is defined by an azimuthal angle θ, wherein each radial cut has an anterior end and a posterior end extending from an inner radius "$r_i$" to an outer radius "$r_o$", with both "$r_i$" and "$r_o$" being measured from the visual axis, with the weakened stromal tissue being responsive to an intraocular pressure for surgically reshaping the cornea.

12. A method as recited in claim 11 wherein the pattern of radial cuts is formed from eight cuts situated about the visual axis, wherein each cut is 45 degrees from an adjacent cut.

13. A method as recited in claim 11 wherein the pattern of radial cuts is formed from twelve cuts situated about the visual axis, wherein each cut is 30 degrees from an adjacent cut.

14. A method as recited in claim 11 wherein the pattern of radial cuts is formed from sixteen cuts situated about the visual axis, wherein each cut is 22.5 degrees from an adjacent cut.

15. A method as recited in claim 11 wherein the pattern of radial cuts is formed from two sets of at least three cuts, and wherein the sets are diametrically opposed from one another.

16. A method as recited in claim 15 further comprising the step of moving the focal spot within the operational volume to create a plurality of cylindrical cuts, wherein each cylindrical cut is made on portions of a respective cylindrical surface, wherein the respective cylindrical surfaces are concentric and are centered on the visual axis of the cornea, and further wherein each cylindrical surface has an anterior end and a posterior end.

17. A method as recited in claim 16 wherein the portions of the cylindrical surfaces subjected to LIOB define diametrically opposed arc segments wherein each arc segment extends through an arc in a range between five degrees and one hundred and sixty degrees.

18. A method as recited in claim 17 wherein the radial cuts intersect the cylindrical cuts.

19. A method as recited in claim 16 wherein the radial cuts and the cylindrical cuts are non-intersecting.

20. A method for performing intrastromal ophthalmic laser surgery, wherein the cornea defines a visual axis and has a thickness "T", and wherein the method comprises the steps of:

generating a pulsed laser beam, wherein the duration of each pulse in the beam is less than approximately one picosecond;

directing and focusing the beam onto a series of focal spots in the stroma for Laser Induced Optical Breakdown (LIOB) of stromal tissue at each focal spot to weaken stromal tissue by redistributing biomechanical forces in the stroma; and selecting a plurality of unconnected cuts from the group consisting of (a) a first plurality of unconnected cylindrical cuts made on portions of cylindrical surfaces concentric on a first axis parallel to the visual axis and a second plurality of cylindrical cuts made on portions of cylindrical surfaces concentric on a second axis parallel to the visual axis and opposite the first axis, (b) a centered plurality of unconnected cylindrical cuts concentric on the visual axis, and (c) a plurality of unconnected radial cuts, wherein each plurality of cuts has a posterior end and an anterior end, with the posterior end of each cylindrical cut being located in the stroma less than approximately 0.9 T from an anterior surface of the eye, with the anterior end of each cylindrical cut being located in the stroma more than at least eight microns in a posterior direction from Bowman's capsule in the cornea, with the posterior end of each radial cut being located in the stroma within less than approximately 0.9 T from the anterior surface of the eye, and with the anterior end of the radial cut being located in the stroma more than at least eight microns in a posterior direction from Bowman's capsule, wherein each radial cut extends from an inner radius "$r_i$" to an outer radius "$r_o$", with both "$r_i$" and "$r_o$" being measured from the visual axis, and wherein each radial cut has a thickness of approximately two microns, is made coplanar with the visual axis, and is defined by an azimuthal angle θ; and moving the focal spot in the stroma to create the selected plurality of unconnected cuts to remove an insignificant amount of tissue to substantially maintain the integrity of the cornea, with the weakened stromal tissue being responsive to an intraocular pressure for surgically reshaping the cornea.

* * * * *